(12) United States Patent
Arkoff et al.

(10) Patent No.: US 12,712,071 B1
(45) Date of Patent: Aug. 18, 2026

(54) OPERATING ROOM MANAGEMENT SYSTEM WITH MOBILE APPLICATION

(71) Applicant: OneSource Solutions International, Inc., Sudbury, MA (US)

(72) Inventors: Harold Arkoff, Sudbury, MA (US); Vedran Jukic, Trieste (IT)

(73) Assignee: OneSource Solutions International, Inc., Sudbury, MA (US)

( * ) Notice: Subject to any disclaimer, the term of this patent is extended or adjusted under 35 U.S.C. 154(b) by 0 days.

(21) Appl. No.: 19/330,953

(22) Filed: Sep. 17, 2025

Related U.S. Application Data

(63) Continuation-in-part of application No. 19/221,392, filed on May 28, 2025, now Pat. No. 12,464,027.

(51) Int. Cl.
*G16H 40/20* (2018.01)
*G06F 3/14* (2006.01)

(52) U.S. Cl.
CPC ........... *G16H 40/20* (2018.01); *G06F 3/1454* (2013.01)

(58) Field of Classification Search
CPC .............................. G16H 40/20; G06F 3/1454
USPC .............................................................. 705/2
See application file for complete search history.

(56) References Cited

U.S. PATENT DOCUMENTS 4,937,743 A * 6/1990 Rassman .......... G06Q 10/06314 345/441
5,842,173 A * 11/1998 Strum ................... G16H 40/67 705/2
5,903,845 A * 5/1999 Buhrmann ............ H04M 3/432 455/461
5,933,778 A * 8/1999 Buhrmann ............. G06Q 30/02 455/445
5,970,466 A * 10/1999 Detjen ............. G06Q 10/06314 705/2
6,674,449 B1 * 1/2004 Banks .................. A61B 5/7435 715/740
8,762,190 B1 * 6/2014 Solomon .............. G06Q 10/109 705/7.12
11,532,393 B2 * 12/2022 Arkoff ................... G16H 40/67
12,327,634 B2 * 6/2025 Arkoff .................. G06F 21/602
2002/0040313 A1 * 4/2002 Hunter ................... G06Q 10/06 705/7.13
2002/0165732 A1 * 11/2002 Ezzeddine ............. G16Z 99/00 705/2
2003/0066032 A1 * 4/2003 Ramachandran ... G06F 3/04847 715/234
2006/0004605 A1 * 1/2006 Donoghue ............ G06Q 10/10 705/2
2006/0053034 A1 * 3/2006 Hlathein ................ G06Q 10/06 705/2
2006/0105301 A1 * 5/2006 Chriss .................. G09B 21/006 340/286.07
2006/0138211 A1 * 6/2006 Lubow ................... G16H 40/63 235/382

(Continued)

*Primary Examiner* — Michael Tomaszewski
(74) *Attorney, Agent, or Firm* — IP Consulting Group; Michael Razavi; Alfred F Hoyte, Jr.

(57) ABSTRACT

An Operating Room Management System (ORMS) for facilitating the efficient and optimal organization of hospital medical personnel and resources runs on local and remote servers and comprises a real-time updated daily schedule which is displayed on digital whiteboards and other displays throughout the hospital. The schedule display simplifies the crucial information concerning common hospital concerns and permits quick, accurate decision making on the part of the hospital medical personnel and administrators.

29 Claims, 11 Drawing Sheets

(56) References Cited

U.S. PATENT DOCUMENTS

2008/0175104 A1* 7/2008 Grieb .................. G06Q 10/109 368/29
2010/0082368 A1* 4/2010 Gecelter ................ G16H 40/20 705/3
2010/0305970 A1* 12/2010 McLaren ............... G16H 10/60 705/3
2010/0306858 A1* 12/2010 McLaren ................ G16Z 99/00 726/28
2010/0332255 A1* 12/2010 Rotunda ................ G16H 40/20 715/753
2013/0066647 A1* 3/2013 Andrie ................... G16H 20/40 705/2
2013/0103768 A1* 4/2013 Freebeck ................ H04L 51/56 709/204
2013/0204635 A1* 8/2013 Okumura ............... G16H 40/20 705/2
2013/0253339 A1* 9/2013 Reyes .................... G06Q 10/06 600/549
2013/0257716 A1* 10/2013 Xin ....................... G06F 1/3215 345/156
2014/0067413 A1* 3/2014 Ghivizzani ............ G16H 40/20 705/2
2014/0108023 A1* 4/2014 Arkoff .................. G06F 21/602 705/2
2015/0242821 A1* 8/2015 Arkoff ............... G06Q 10/1097 705/2
2015/0286788 A1* 10/2015 Arkoff ................... G16H 40/20 705/2
2016/0323417 A1* 11/2016 Spear ..................... G06Q 10/06
2021/0050104 A1* 2/2021 Arkoff ................... G16H 40/67
2022/0406448 A1* 12/2022 Naruse ................... H04N 7/181
2023/0090000 A1* 3/2023 Arkoff ................ G06F 21/6254 705/2
2024/0265321 A1* 8/2024 Neubauer ...... G06Q 10/063116

* cited by examiner

OPERATING ROOM MANAGEMENT SYSTEM WITH MOBILE APPLICATION

CROSS-REFERENCE TO RELATED APPLICATIONS

This application is a Continuation in Part of application Ser. No. 19/221,392 filed May 28, 2025, which is a continuation in part of application Ser. No. 17/993,765 filed Nov. 22, 2023, now U.S. Pat. No. 12,327,634, which is a Continuation of application Ser. No. 16/812,282 filed on Mar. 7, 2020, now U.S. Pat. No. 11,532,393, which is a CIP of application Ser. No. 13/651,058 filed on Oct. 12, 2012, now abandoned.

FEDERALLY SPONSORED RESEARCH

Non applicable

SEQUENCE LISTING OR PROGRAM

Non applicable

FIELD OF THE INVENTION

This application relates to healthcare facility management software and more particularly to operating room management system (ORMS) software having an interacting mobile phone application.

BACKGROUND

Hospitals and other healthcare facilities providing surgical services must coordinate a myriad of resources, medical personnel, and hospital staff to provide optimum and efficient care to their patients. Information about status of these resources and the facilities' patients must be updated constantly and be available to the relevant medical personnel and facility staff in the operating rooms (ORs) where the surgical services are delivered, in other ancillary rooms of the facility, and to medical personnel and facility staff who may be in remote locations. Particular medical personnel or facility staff members may need to be alerted with respect to the updated status of particular resources or patients and may need to provide updates to the information displayed from where ever they are located.

Modern hospitals are complex, technologically sophisticated organizations having sometimes thousands of employees, doctors, nurses, medical technicians and administrators, with critical life or death decisions being made regularly—and sometimes having to be made abruptly and quickly. Up-to-date, easily apprehended information about the personnel and resources available can make a difference. And even when critical decisions are not at stake, the recent increases in the cost of health care have made it imperative to use the facility personnel and resources as efficiently as possible.

U.S. Pat. No. 5,842,173 to Strum et al., issued for "Computer-Based Surgical Services Management System," describes a complex database running on a server and display system to coordinate surgical services at a medical center, but it is updated only periodically, not continuously. It also does not provide for remote notification and interaction by the medical center personnel.

U.S. Pat. Application Nos. 2010/0306858, 2010/0305970, 2010/0305971, 2010/0305972, and 2010/0305973 to McLaren et al. describe central medical information systems with interacting mobile applications. The described systems, however, are based on a typical medical case or patient focused database and display, rather than systems focused on the status and coordination of medical facility resources.

U.S. Pat. No. 7,657,445 to Goux describes a system for managing healthcare facility resources, but it is specifically focused only on tracking the number of hours provided per patient rather than on the coordination of the large number of resources used by a typical healthcare facility or giving medical personal the information they need to make quick and accurate decisions.

SUMMARY

In accordance with the present disclosure, embodiments of a system, method, and apparatus are described which eliminate or ameliorate the problems and disadvantages associated with previous systems, methods, and apparatuses.

According to a particular embodiment, a system of servers is provided, which communicate data in real time with white boards stationed in the operating rooms of a healthcare facility. Medical personnel and healthcare facility staff members can view the formatted data on a white board and input new or revised data directly on the white board or at an input station near the white board.

Further in this embodiment, mobile phones carried by medical personnel and healthcare facility staff run applications enabling the real time display of data communicated by the servers and allowing the input of new or revised data into these mobile phones to be transmitted to the servers and displayed when appropriate on whiteboards and other displays throughout the facility. The mobile phone applications further permit the alerting of specific personnel, other mobile phone carriers and throughout the facility.

BRIEF DESCRIPTION OF THE DRAWINGS

FIG. 7A is an illustration of a stop light alert icon in an embodiment.

DETAILED DESCRIPTION

Figure 1:
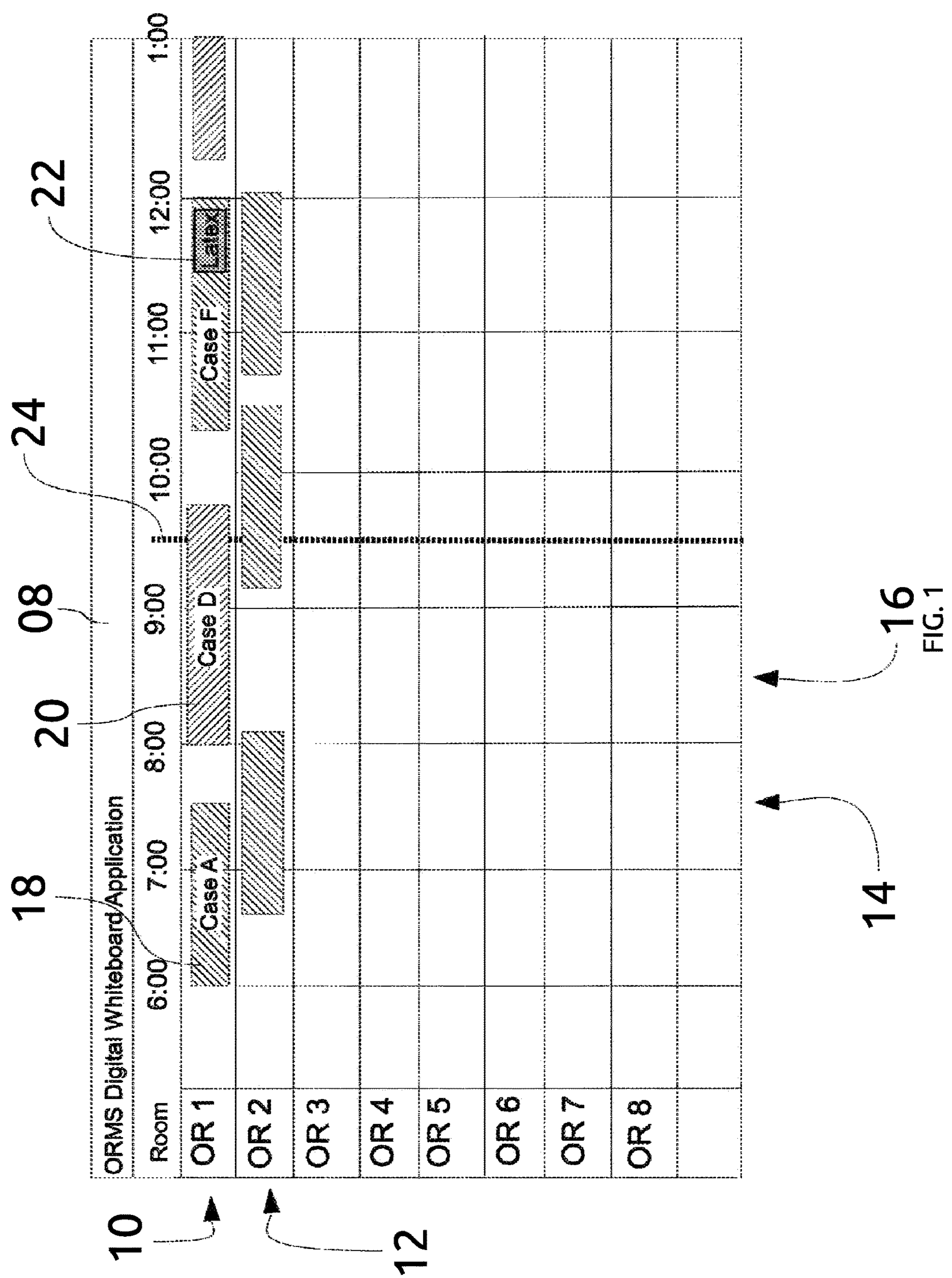
FIG. 1 is an illustration of a hospital daily schedule display on an operating room digital white board.

In an embodiment of the invention, FIG. 1 is an example illustration of a daily schedule 8 for the operating rooms of a hospital or healthcare facility. Schedule 8 would be displayed on a multiplicity of digital whiteboards in various places of the healthcare facility such as the anterooms of the operating rooms. The rows of schedule 8 correspond to different operating rooms of the facility. For example, rows 10 and 12 correspond to OR 1 and OR 2 respectively as indicated. The columns, for example 14 and 16, correspond to the time of use of the operating rooms by the patient cases undertaken. The current time of day is indicated by a vertical line 24 through schedule 8.

The patient cases scheduled are depicted as shaded or colored blocks, for example 18 and 20, extending for the length of time they will occupy the operating room. Text within the blocks, such as shown 18 and 20, provide details of the cases such as the name of the patient and the procedure planned. The type of shading or different colors of the blocks 18 and 20 indicate the case status and current location of the patient. Alerts concerning the case such as pertinent allergies may also be indicated by a separate shaded or colored area with a case block as illustrated at 22 for example. Such a color-coded, resource-focused schedule in combination with a display of simplified information is unique in the setting of a hospital or health-care facility and is surprisingly effective in providing a comprehensive picture of the data needed to optimally organize the doctors, nurses and other health care personnel, and the resources they need, and further, uniquely and surprisingly enhances the making of quick, accurate decisions in critical situations.

Figure 2:
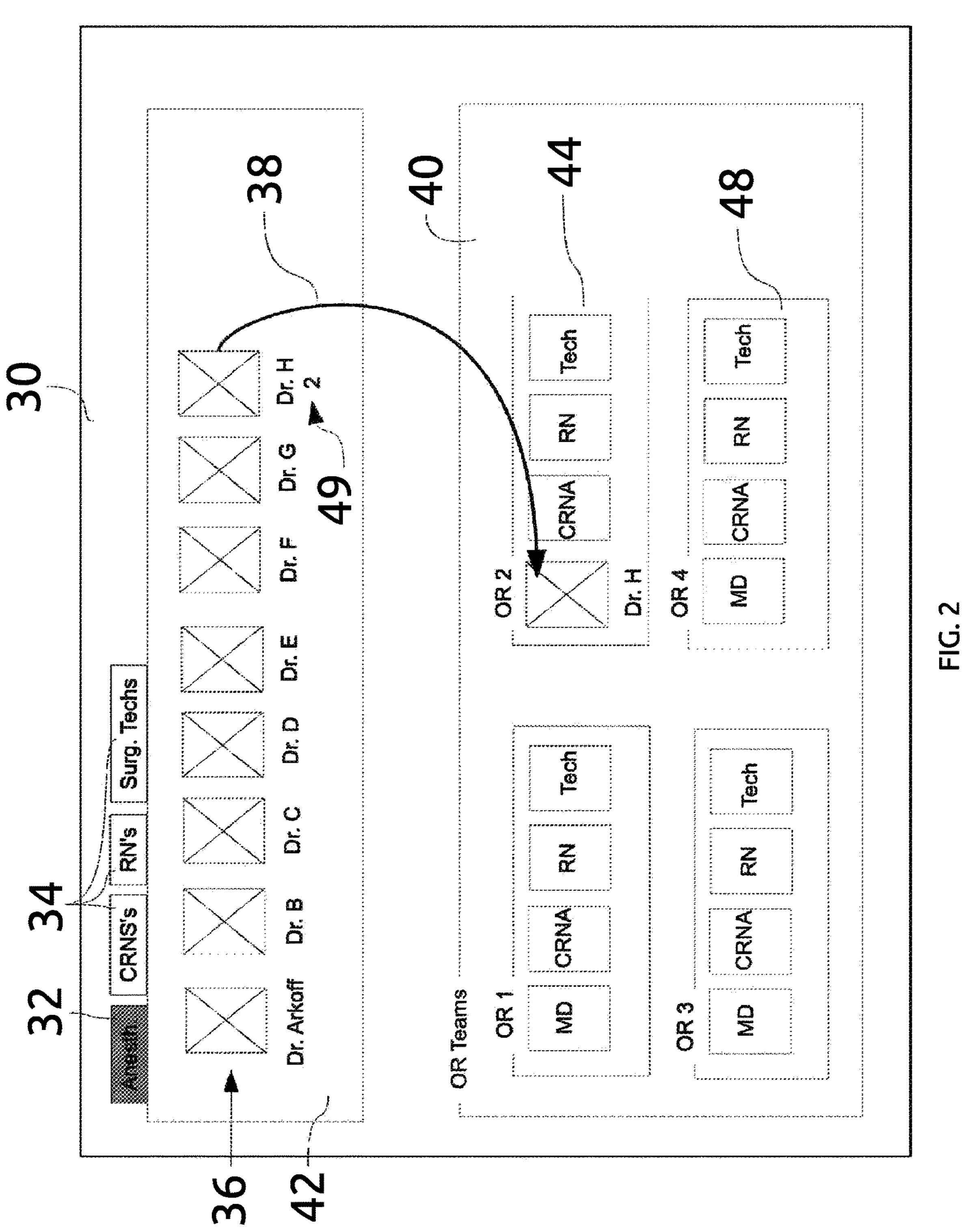
FIG. 2 is an illustration of the team building display on an operating room digital whiteboard in an embodiment of the invention.

Surgical teams can be formed and assigned easily using a display 30 of individual health care facility personnel organized by specialty and work shifts such as illustrated in FIG. 2. Medical personnel by specialty are shown at the display top 42. In this example, the group of anesthesiologists have been selected to be displayed by highlighting tab 32. Once selected, the anesthesiologist's names and pictures are displayed in a row as indicated 36. Alternatively, if any of tabs 34 were selected and thus highlighted, the corresponding group of medical personnel would be displayed at the top 42.

To form a particular team, individual personnel available to work that day are dragged and dropped to the appropriate position in the chosen team in lower box 40. As an example, in FIG. 2, Dr. H has been dragged and dropped on the MD position on OR 2 (numbered 44) as indicated by arrow 38. In some instances, personnel can be assigned to more than one teams. In such a case, the picture and name of the person remains in the top row until he has been assigned the maximum number of times. This is shown by example with the photo of Dr. H remaining in the top row 36 at the same time his photo is displayed as a part of OR 2 (numbered 44). The maximum number of times a person can be assigned to a team is typically determined on an individual basis.

Once formed, the teams are dragged and dropped on particular patient cases and then displayed on the main schedule 8 on whiteboards and other displays throughout the facility. The dragging and dropping process can be carried out directly on the whiteboard or other display using a method of digital input such as computer mouse or stylus, or to facilitate quick and easy input to the display on a digital whiteboard, a user can use for example a tablet computer communicating with the whiteboard via a bluetooth or other wireless connection and displaying a facsimile of the team building screen.

A suitable digital whiteboard capable of displaying the schedule 8 is the Hitachi Starboard FXTRIO Interactive Whiteboard available from Hitachi Solutions America, Ltd., 601 Gateway Blvd. Suite 100, South San Francisco, CA, although many other digital whiteboards or other computer-controlled display systems can be used. If the Starboard FXTRIO digital whiteboard is used, then a software interface such StarBoard Software also available from Hitachi Solutions can be used to facilitate the creation and modifications of schedule 8.

Figure 3:
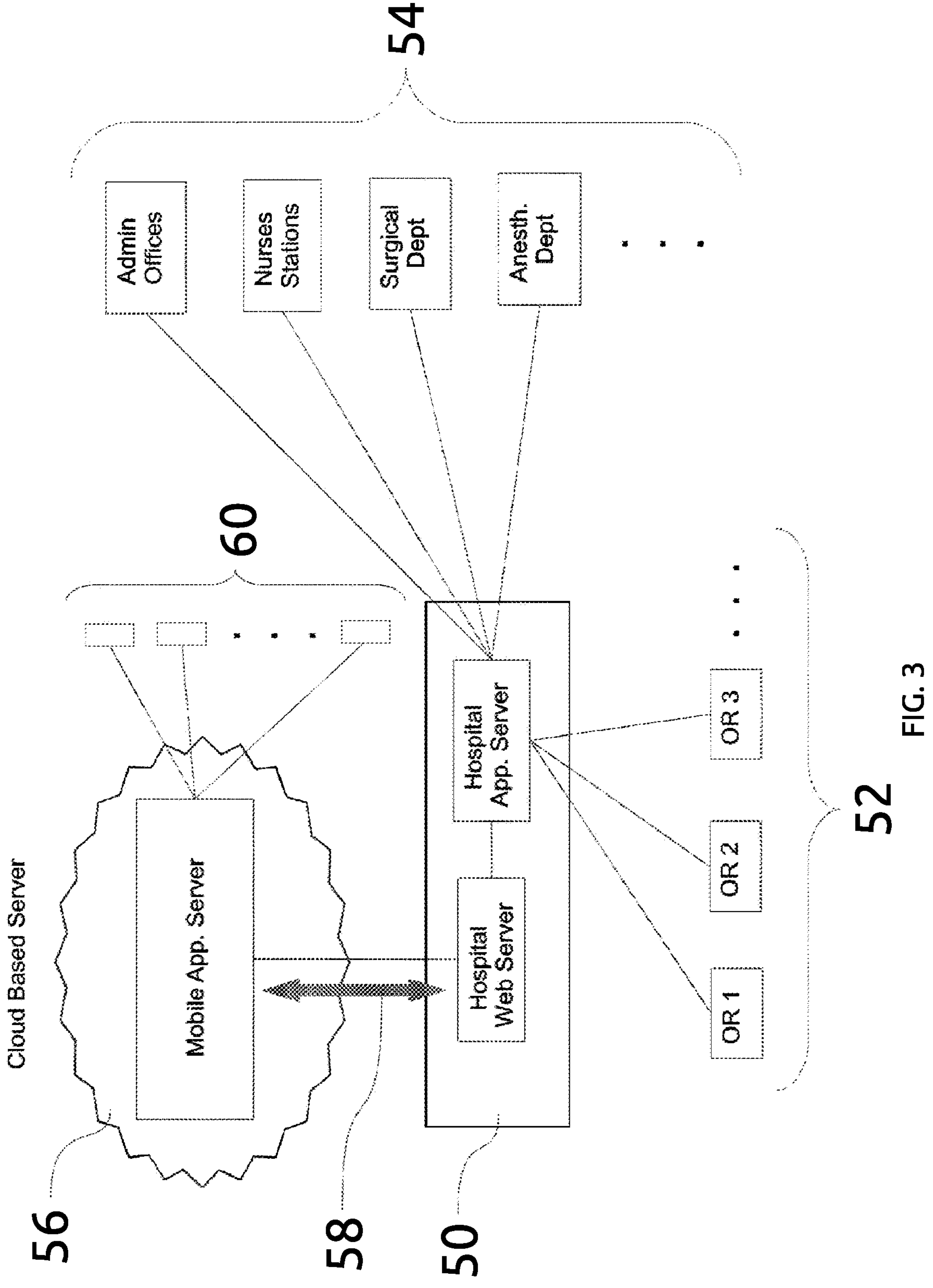
FIG. 3 is a block diagram detailing the arrangement of specific servers in an embodiment.

FIG. 3 is a block diagram overview of the overall system running the ORMS software in an embodiment. Local server 50 receives, stores, calculates, and transmits data in forms such as schedule 8 to the facility operating room sites 52 and facility offices and stations 54. Schedule 8 and other data may be displayed on for example digital whiteboards, desktop displays, tablet computers, or mobile devices depending on the needs of the site or office. The local server 50 is in continual, real time communication with cloud-based server 56 which is not physically located at the healthcare facility. In an alternative embodiment, all variable patient, case and resource data is maintained on the local and cloud-based servers and downloaded to the individual whiteboards, displays, stations, or departments, but calculation and formatting of the schedule and determination of alerts is done by applications or software modules running on the PC's or embedded computers associated with each individual whiteboard, display, station, or department.

All substantive data on local server 50 is continually backed up on cloud-based server 56 and vice versa as indicated by arrow 58. In this embodiment, the data continually backed up includes all current information about the patient cases the hospital has undertaken and the information about the health care facility resources and personnel necessary to calculate and display the schedule.

Cloud-based server 56 transmits a facsimile of the schedule 8 and other data to apps on the mobile phones 60 of doctors and other relevant health care personnel. Also, via this path, alerts can be texted or otherwise transmitted to specific personnel. An alert is short message or datum of high importance and urgency. Alerts may for example indicate an unexpected problem or delay with a particular patient or case, or patient overcrowding at a particular stage or location within the facility. Alerts can be manually triggered for example by personnel at any of the offices and stations 54, or automatically triggered by one of the servers based on calculations from data input by personnel at for example operating room sites 52 or offices and stations 54. Such automatically triggered alerts can be fixed as a part of the system design or can be customized by various healthcare facility personnel.

An alert displayed on one or more mobiles phone 60 can be responded to immediately by a user or users and data in the response displayed in real time on one or more of the digital white boards near the OR's 52, station or office desktop displays 54 or other displays in the healthcare facility or in the overall system. The response can be a direct change in the displayed schedule or used to automatically calculate a change in the schedule which is then displayed. Personnel at these sites can then make further adjustments to the schedule or input other data accordingly. Correspondingly, any changes in the schedule such as illustrated FIG. 1 will be transmitted in real time to the other sites and the apps on the mobile phones 60. Having the capability of alerts for mobile users which can be responded to by transmitting schedule changes to the overall system is a unique and surprisingly effective method of optimizing the resource usage of the hospital or health-care facility.

Local server 50 can be implemented using a standard PC with for example an Intel Ivy Bridge microprocessor running the Windows 7 operating system. Of course Apple or UNIX-based computers, among others, could also be used as would be obvious to engineers with ordinary skill in the art. Cloud-based server 56 can be implemented for example using a commercial cloud computing service such as Amazon Web Services available at URL http://aws.amazon.com/ or using standard PCs at a remote location. Software development for the servers and the station or desktop modules can be done in Visual Basic with the Microsoft Visual Studio development environment although myriad other programming languages and development environments can be used. The displays such as illustrated in FIGS. 1 and 2 are typically implemented using an internet browser such as Firefox and coded in HTML although other browsers or direct implementation in Visual Basic or many other programming languages and development environments known to software engineers with ordinary skill in the art can be used.

Figure 4:
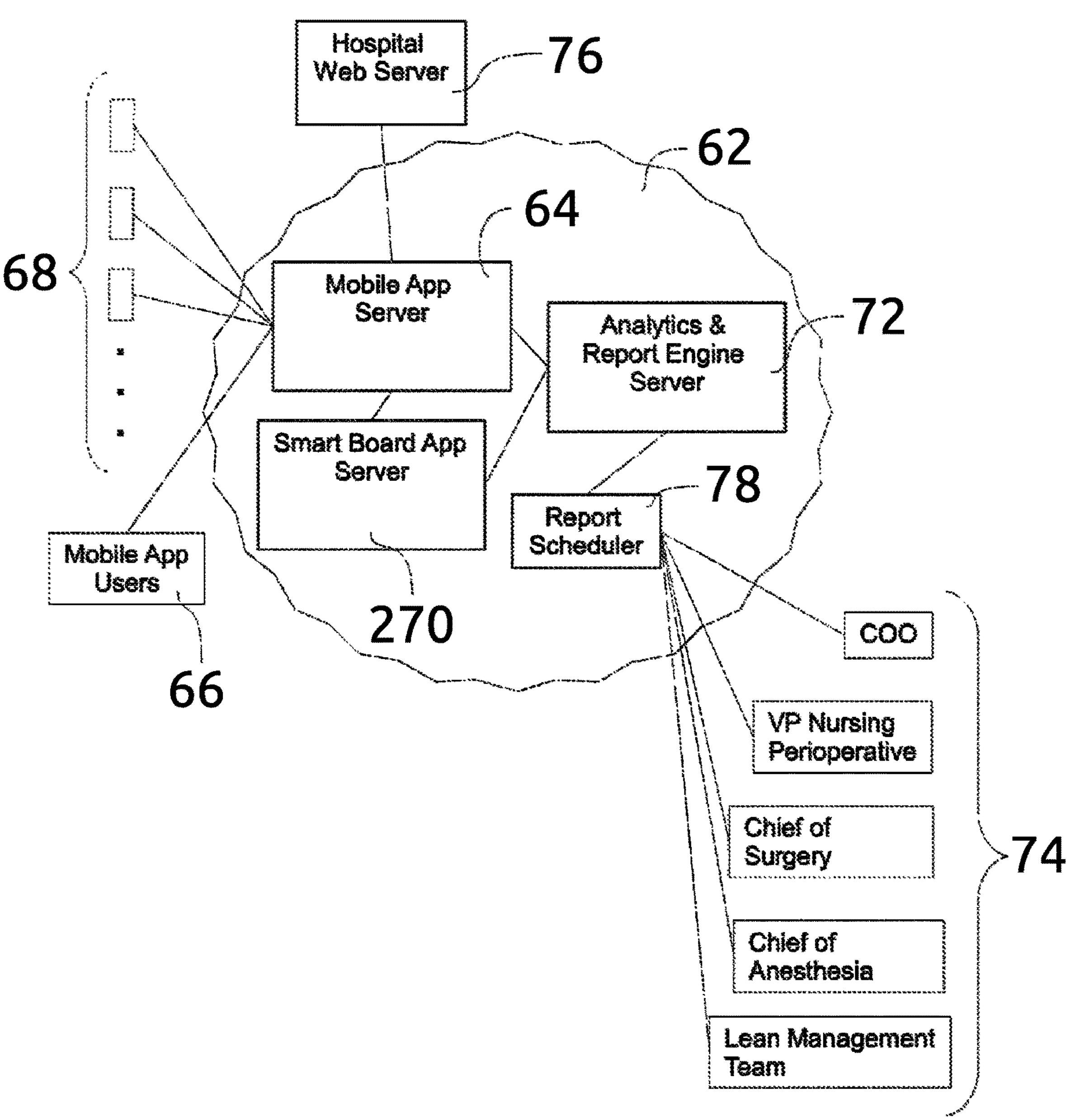
FIG. 4 is a block diagram illustrating the arrangement of specific servers within the cloud server in another embodiment of the invention.

FIG. 4 is a block diagram of an arrangement of application-specific servers at remote cloud server 62 in another embodiment of the invention. In this embodiment, cloud server 62 includes a mobile applications server 64 which communicates directly with the mobile phones of users running an app 66. The mobile applications server can also send and receive SMS text messages to the mobile phones 68 of users whose phones do not have the mobile app capability.

Cloud server 62 also runs the digital white board application server 70. Both the digital white board server 70 and the mobile applications server 64 communicate data directly to the analytics and report engine server 72 which analyzes said data and creates appropriate reports. Said reports are sent periodically via the report scheduler 78 to the appropriate personnel, collectively 74, at the hospital. Generally, realtime data is communicated to and from the hospital display locations, stations, departments, and offices via the hospital web server 76.

Figure 5:
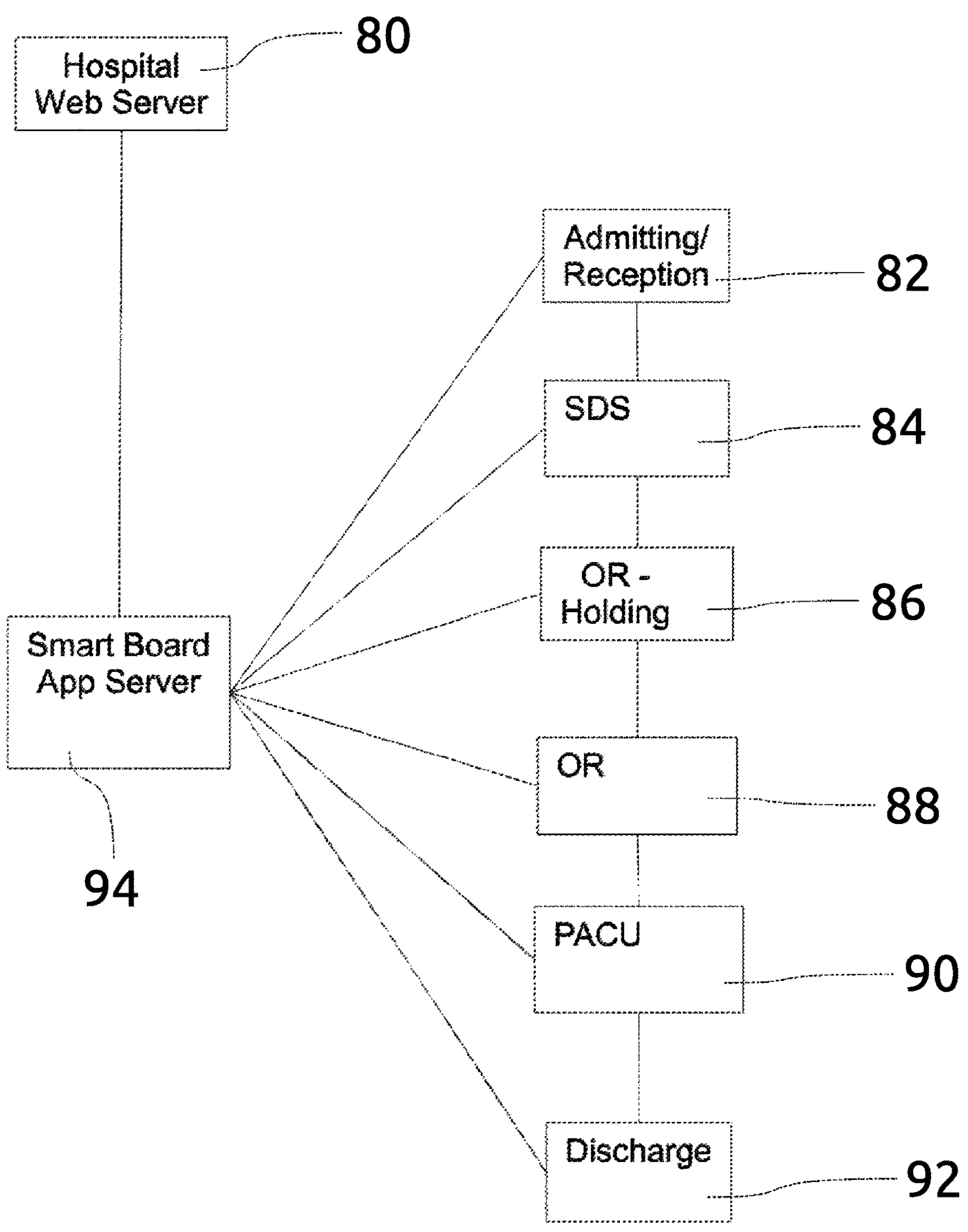
FIG. 5 is a block diagram illustration of patient movement through the hospital and corresponding data entry.

FIG. 5 is a block diagram showing patient movement through the health-care facility. In this embodiment, when a patient enters the reception area 82, his arrival is input to the hospital web server 80 by admitting personnel and his case is displayed on the OR schedule such as illustrated 18 and 20 for example on FIG. 1. As the time for the patient's operation approaches, he moves to SDS 84 and then to the OR holding area 86.

At each department or station, the patient's progress is updated on the OR schedule by the staffing personnel who typically input the data using desktop PCs or tablet computers. The ORMS software module running on the desktops PCs or tablet computers is typically customized for each department or station.

At the appropriate time and when the surgical team and all resources are ready, the patient moves to the OR 88 and the operation is performed by the surgical team. After the operation is complete, the patient moves to the PACU 90 and when ready the discharge area 92 where the patient may fill out a survey which he inputs directly to the hospital web server 80.

Figure 6A:
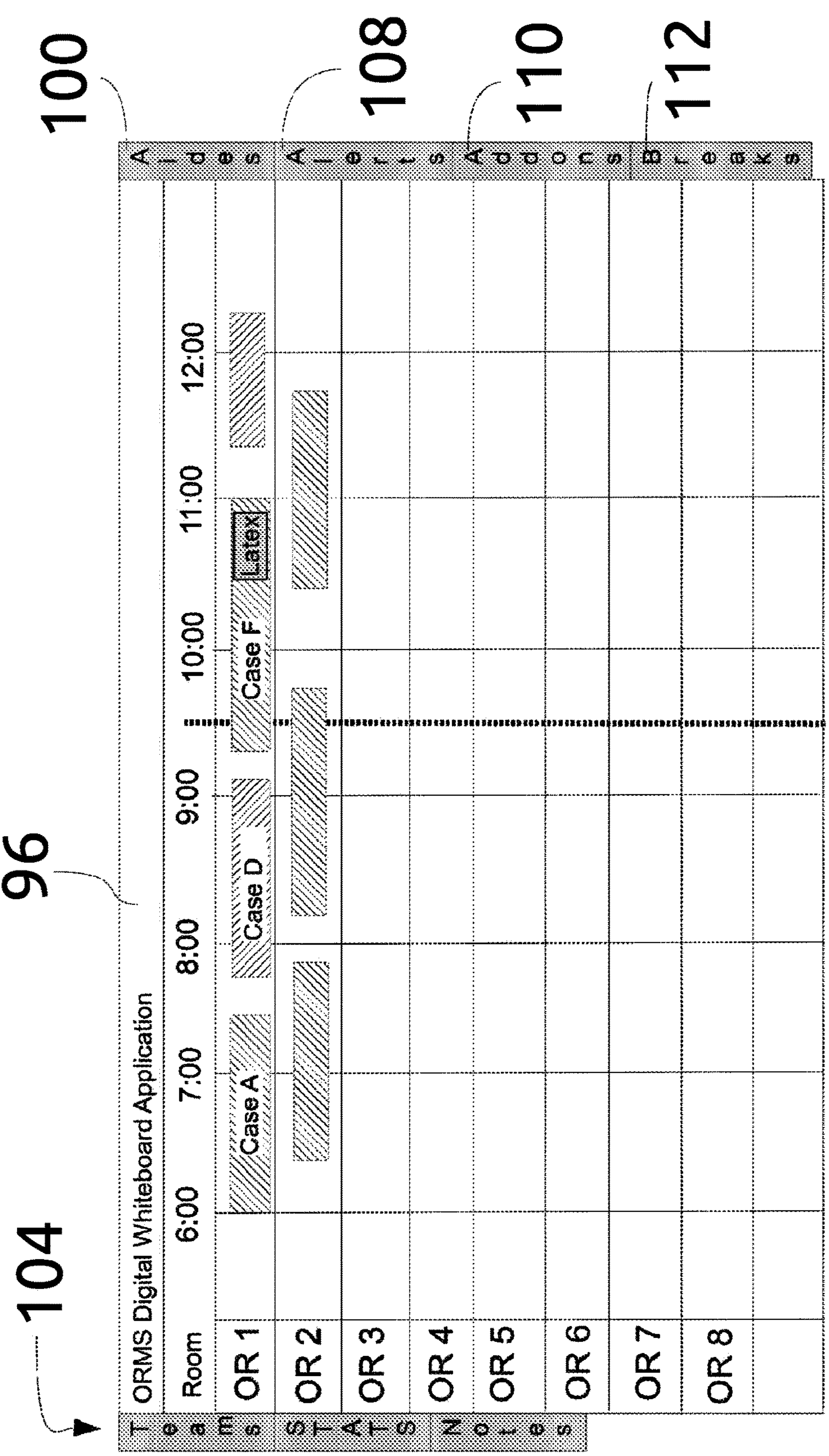
FIG. 6A is an illustration of tabs on the daily schedule display indicating the availability of viewable side panels.
Figure 6B:
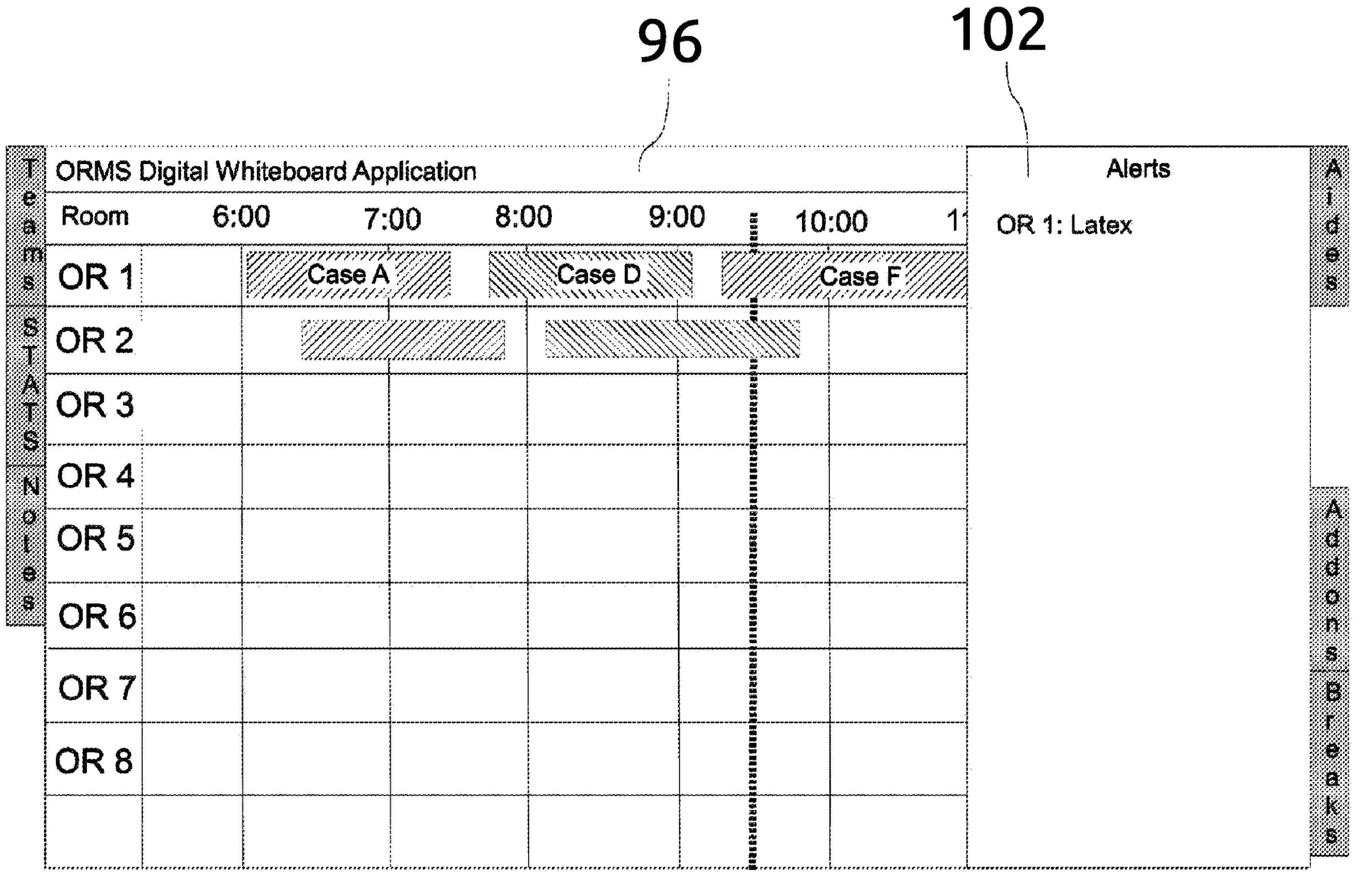
FIG. 6B is an illustration of a displayed side panel on the daily schedule display.

In another embodiment, FIGS. 6A to 6D illustrate dockable slide-out panels on the OR schedule. In FIG. 6A, Tabs 100, 108, 110, and 112 arrayed on the right hand side of the daily schedule display 96 have labels indicating available panels with pertinent information. Other such tabs, as indicated at 104, are arrayed on left hand side of schedule 96. In FIG. 6B, the Alerts tab 108 has been selected using for example, a computer mouse or touch screen entry, and the alert panel is displayed 102 while Alerts tab 108 temporarily disappears.

Information or notes can be added directly to panel 102 with digital input, for example, keyboard or computer mouse, and this information or notes is reproduced on some or all schedule displays through the hospital depending on user-selectable parameters. In an alternative embodiment, information or notes can be written directly in panel 102 area in an analog manner, that is, with a stylus or even a finger, and this information or notes is reproduced on some or all schedule displays throughout depending upon selectable parameters.

Figure 6C:
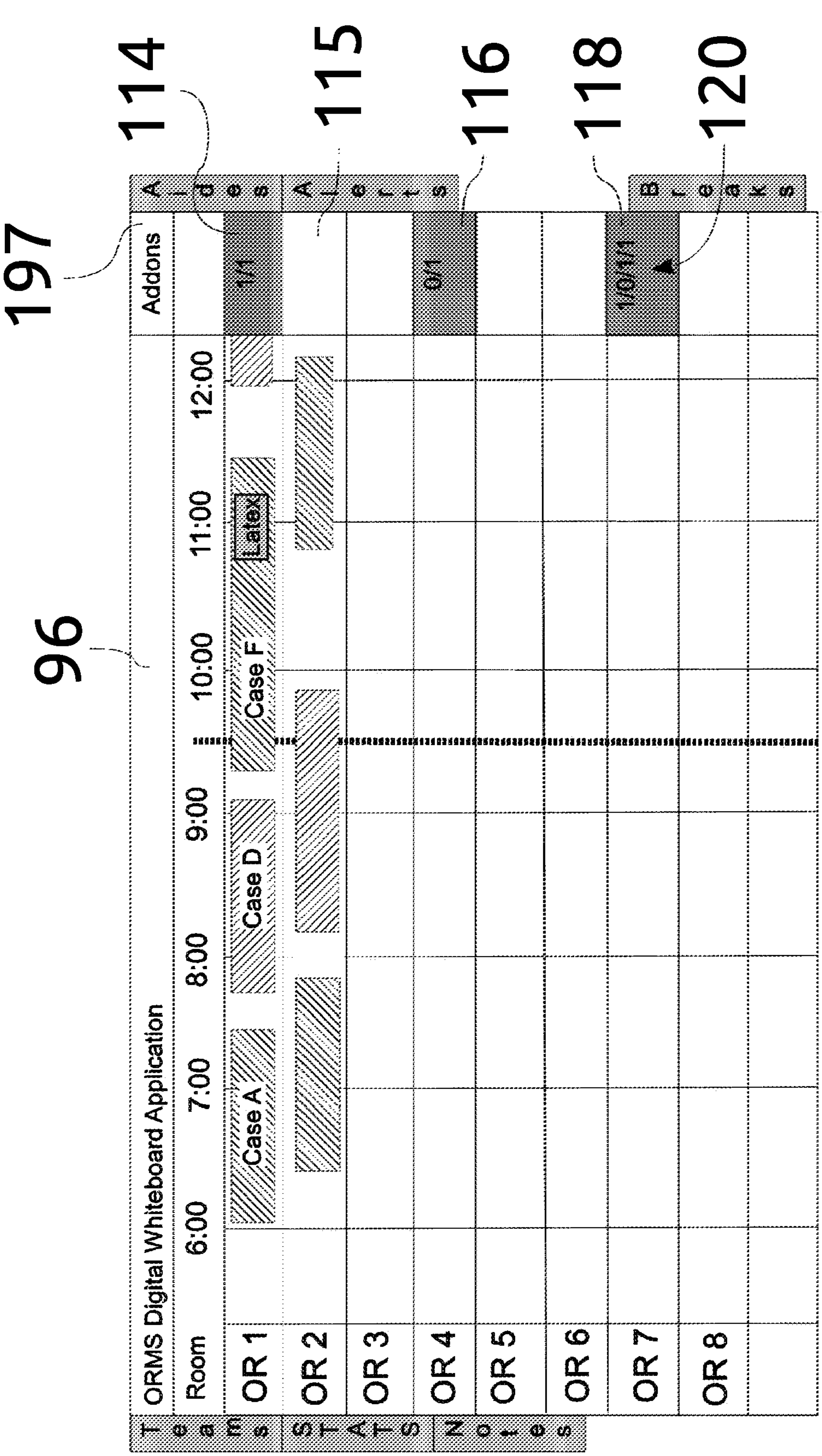
FIG. 6C is an illustration of a second displayed side panel on the daily schedule display.

FIG. 6C is an illustration of the schedule 96 when the Addons tab 110 has been selected such that the Addons panel 97 is displayed. An addon is a case which is newly added after the schedule for the day is created, with corresponding allocation of the hospital personnel and resources, and which is expected to run past a hospital's employee shift change time. Another type of addon is a case which was on the daily schedule when created but is delayed or running late due to unforeseen circumstances and is thus expected to run past the time of one or more employee shift changes. It is important for hospital managers and administrators to know quickly and accurately how many addon cases they have and through what shift changes they will go so they can make sure they will have the personnel present and resources on hand to cover these cases. A hospital or other health-care facility may have several shift change times when nurses, technicians, and other medical and administrative personnel end or start their work day. For example, a hospital might generally have four shift change times at 3:00 PM, 3:30 PM, 5:00 PM, and 7:00 PM.

For example, in FIG. 6C, block 114 is highlighted to indicate there is one or more addon cases in OR 1. Block 116 is highlighted to indicate there is one or more addon cases in OR 4. And block 118 is highlighted to indicate there is one or more cases in OR 7. When no addon cases have been added to the schedule for an operating room, the corresponding addon block is not highlighted, for example, 115, and remains the neutral color of the schedule, typically white.

The highlighted addon blocks, 114, 116, and 118, contain a simple symbolic code, such as seen at 120 for example, which indicates how many addon cases are scheduled for the corresponding OR and the shift change times they are expected to run past. In this embodiment, the symbol 1 is used in the code to indicate an addon case that will run past a shift change. The position of the symbol 1 in the code indicates which shift change the addon case will run past. So in the case of a hospital with four employee shift changes at 3:00 PM, 3:30 PM, 5:00 PM, and 7:00 PM such as described hereinabove, the code would have up to four positions, reading from left to right. So for example, the code 120 has a 1 in first position indicating a case which will run past the earliest shift change time of concern, 3:00 PM. Then there is the symbol '/' as a separator and then the symbol 0 as a placeholder, indicating that there are no addon cases in OR 7 anticipated to run past the 3:30 PM shift change. Continuing to read from left to right at 120, there is a second '/' and then a 1 indicating that there is an addon case expected to run past the 5:00 PM shift change time. Finally, there is a '/' and a 1 indicating that there is an addon case expected to run past the 7:00 PM shift change. Note, it may or may not be that the addon case running past the 7:00 PM shift change is the same case or a continuation of the same case that is expected to run past the 5:00 PM shift change as described hereinabove.

Thus, the combination of color highlighting 114, 116, and 118, and a simple symbolic code 120, enables a hospital administrator or medical personnel manager to at a glance quickly and accurately determine the additional personnel and resources needed to timely complete, with optimum outcome, the cases the hospital has undertaken. That this combination of color highlighting and an associated simple symbolic code on a comprehensive, real-time updated daily schedule displayed or available to display at a multiplicity of locations throughout the hospital or healthcare facility, provides such facile comprehension of a possibly critical situation at hand, permitting quick and accurate decision making by perhaps a multiplicity of hospital or health-care facility administrators and managers at different locations, is a unique and surprising, perhaps even revolutionary, result.

Figure 6D:
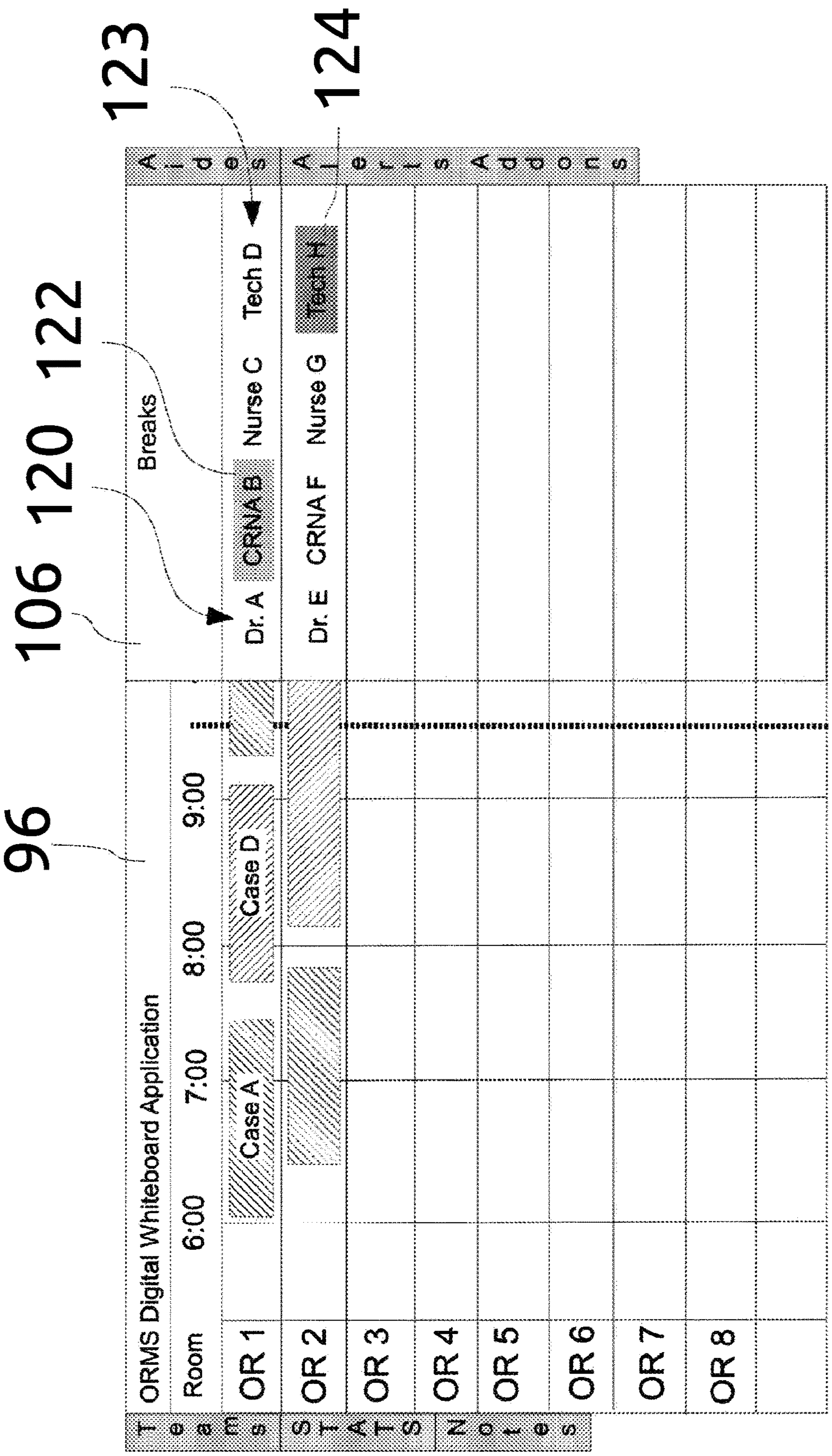
FIG. 6D is an illustration of a third displayed side panel on the daily schedule display.

FIG. 6D is an illustration of the schedule 96 when the Breaks tab 112 has been selected such that the Breaks panel 106 is displayed. A break is a relatively short period during the work shift of a hospital or healthcare facility employee when they are "off-duty", perhaps having a meal or a rest-break. The current break status of an employee is displayed and can be modified in the Breaks panel 106.

The personnel on a particular OR team are displayed in the row corresponding to the OR to which they are assigned such as indicated at 123. The name of team member not on break and working normally, indicated at 120 for example, will have a background of a neutral color, typically the same as the neutral color of daily schedule, typically white. A team member name can be selected, such as by clicking with a computer mouse or tapping with a finger or stylus on a touch-sensitive display, and then the background of the team member name will turn a color, for example 122, understood to indicate they are on break. A team member name can be selected a second time, and the background of their name will turn a second color, for example 124, understood to mean they have returned from break and are now working normally. After a set period, perhaps a few minutes, which can be configured by hospital administrators or other personnel, the second colored background 124 will automatically change back to the original neutral color indicating normal working status 120.

The organizational efficiency and decision making confidence gained by having all this information about the hospital's current patient cases available in a single view display of the daily schedule of the hospital is unique and surprising. However, while the hospital administrators, like the hospital medical personnel, benefit from having available comprehensive information about the hospitals current cases and relevant resources, not every administrator needs to have a continuous view of the schedule display.

Figure 7B:
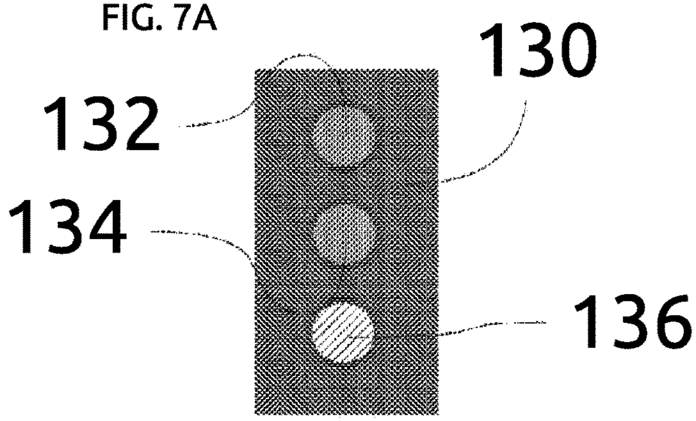
FIG. 7B is an illustration of a stop light alert icon in a small window on the desktop display of an administrator.
Figure 7B:
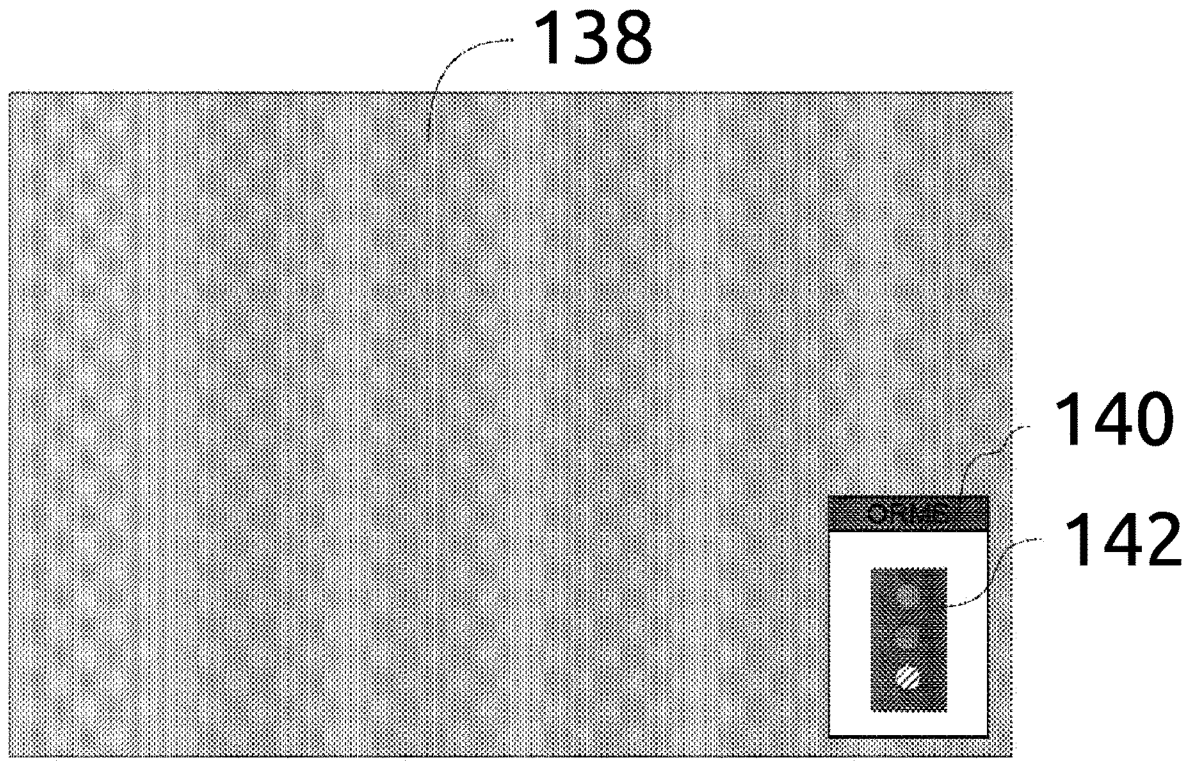

FIGS. 7A and 7B are illustrations of a stoplight icon 130 which can be displayed on the computer desktop display 138 of administrators and at stations where the OR schedule display is not continuously needed. In a fashion similar to the workings of an ordinary traffic light for the control of street traffic, when there are no known problems likely to interfere with hospital's daily schedule as planned, the upper "lights" 132 and 134 would be dimmed and lower "light" 136 would be highlighted, typically green. If an alert condition occurs, which can be manually triggered or automatically triggered by calculation as described hereinabove, then light 136 would be dimmed and upper lights 134 or 132 typically would be yellow or red respectively, depending on the urgency of the alert.

As shown in FIG. 7B, stop light icon 142 would typically be shown in a small window 140 on an administrator's PC desktop 138 but in other embodiments the icon could stand alone on the desktop without a surrounding window or in many other configurations as would be apparent to software engineers of ordinary skill in the art.

Figure 8:
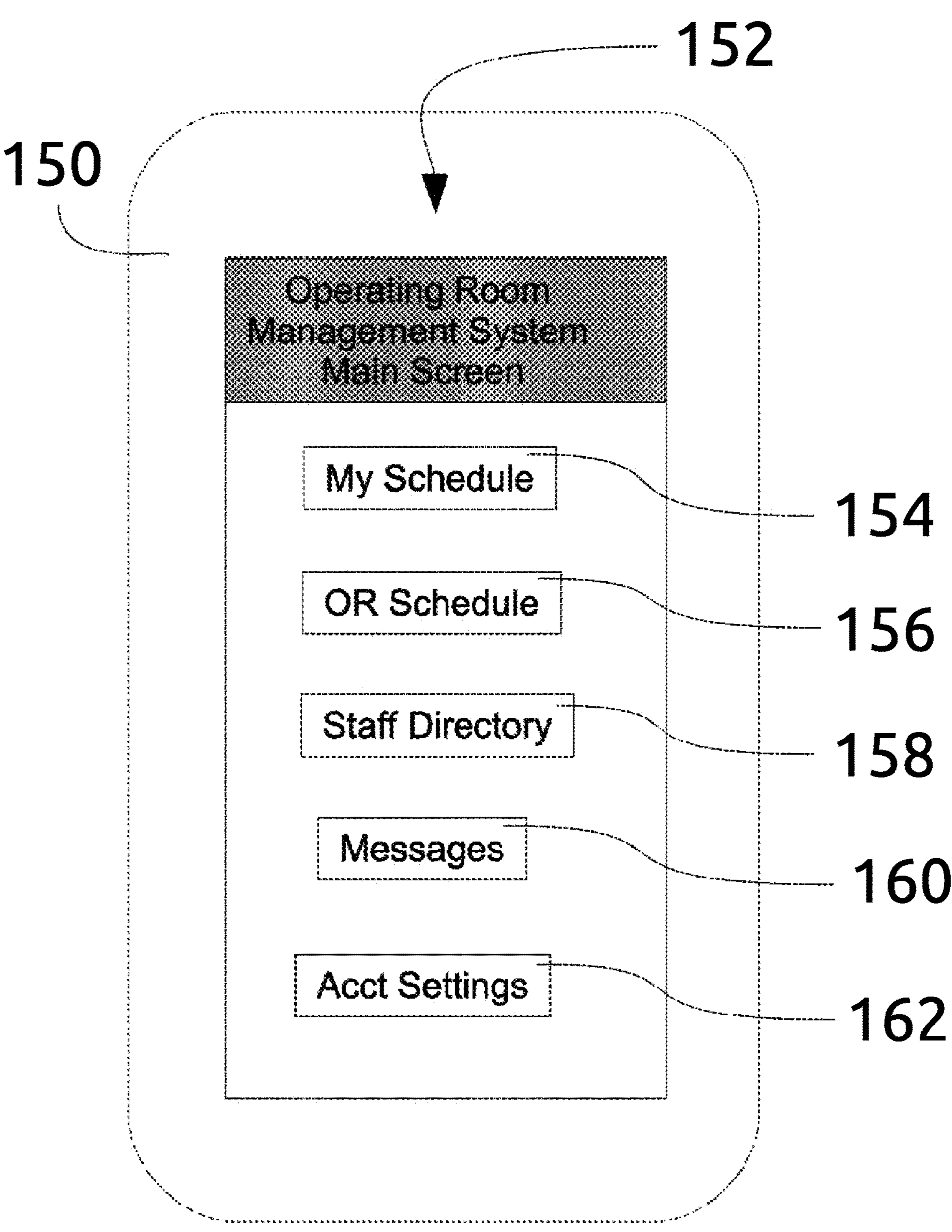
FIG. 8 is an illustration the main navigation display on the smartphone running the ORMS app of an embodiment.

FIG. 8 is an illustration of the main navigation screen of the ORMS app on the smartphone 150 of a user who might typically be a doctor or nurse at the hospital. The smartphone display indicated 152 shows selectable options to display the user's personal schedule 154, the OR daily schedule 156, the staff directory 158, the user's messages 160, and the user's account settings 162.

Although particular embodiments have been described in this disclosure, many other variations and modifications will be apparent to those skilled in the art. Thus the instant invention can be defined and limited only by the below claims.

The invention claimed is:

1. A system for managing the display of a real time daily schedule, said schedule displayed as a series of blocks dynamically affected by real time activities of medical personnel within a healthcare facility and displayed on both whiteboard display devices in operating rooms of said healthcare facility and displays on mobile phones, the system comprising:

a cloud server running a program having a set of data concerning the management of said operating rooms, a digital whiteboard server that receives and processes said set of data for display on said whiteboard display devices, and a mobile applications server that processes said set of data for display on said mobile phones;

a software interface receiving and configuring processed data from said whiteboard server to display said real time daily schedule on said whiteboard display devices in operating rooms;

wherein said software interface configures said whiteboard display devices to display a schedule which changes in response to the real time activities of the medical personnel, and wherein a portion of at least one said blocks is highlighted in a first color, and said software interface is programmed to change said first color to a second color in response to a first condition.

2. The system for managing the display of a real time daily schedule of a healthcare facility according to claim 1 wherein said mobile applications server communicates with at least one mobile phone which runs an application that alerts a mobile phone user.

3. The system according to claim 2 wherein at least one display by said application is of a daily schedule of the user.

4. The system according to claim 1 wherein said display devices receive and display data which is input digitally to said display devices using a tablet computer and said display devices also receive and display data which is input in an analog manner directly on a display surface of the display devices in operating rooms.

5. The system according to claim 1 wherein the display devices are capable of displaying a schedule for teams of healthcare facility personnel, said teams having been formed from a displayed list of healthcare facility personnel.

6. The system according to claim 3 wherein specific data input to said mobile applications server automatically triggers sending an alert to said user.

7. The system according to claim 1 wherein the display devices show breaks taken by said facility employees in realtime.

8. A system for managing the display of a real time daily schedule, said schedule dynamically affected by real time activities of medical personnel within a healthcare facility and displayed on both whiteboard display devices in operating rooms of said healthcare facility in a building and displays on mobile phones, the system comprising:

at least one server running a program having a set of data concerning the management of said operating rooms and a real time daily schedule for said operating rooms in said building;

a whiteboard server and a software interface receiving data from said at least one server and configuring the display of said real time daily schedule on said whiteboard display devices in operating rooms;

wherein said software interface configures said whiteboard display devices to display a schedule which changes in response to the real time activities of the medical personnel, and wherein at least one block is highlighted in a first color and contains a simple symbolic code, and said software interface is programmed to change said first color to a second color in response to a first condition.

9. The system of claim 8 including a mobile applications server receiving, processing, and displaying said schedule on at least one mobile phone.

10. The system for managing the display of a real time daily schedule of a healthcare facility according to claim 9 wherein said mobile applications server communicates with at least one mobile phone which runs an application that alerts a mobile phone user.

11. The system according to claim 8 wherein at least one display by said application is of a daily schedule of the user.

12. The system according to claim 8 wherein said display devices receive and display data which is input digitally to said display devices using a tablet computer and said display devices also receive and display data which is input in an analog manner directly on a display surface of the display devices in operating rooms.

13. The system according to claim 8 wherein the display devices display a schedule for teams of healthcare facility personnel, said teams having been formed from a displayed list of healthcare facility personnel.

14. The system according to claim 10 wherein specific data input to said mobile applications server automatically triggers sending an alert to said user on said at least one mobile phone.

15. The system according to claim 8 wherein the display devices show breaks taken by said facility employees in realtime.

16. A non-transitory computer-readable medium storing instructions that, when executed by one or more processors, cause the one or more processors to:

(a) manage a real time daily schedule for a healthcare facility, said schedule displayed as a series of blocks dynamically affected by real time activities of medical personnel within the healthcare facility;

(b) cause the schedule to be displayed on both whiteboard display devices located in operating rooms of the healthcare facility and on displays of mobile phones;

(c) operate a cloud server that maintains a set of data concerning the management of said operating rooms;

(d) operate a digital whiteboard server that receives and processes said set of data for display on the whiteboard display devices;

(e) operate a mobile applications server that processes said set of data for display on said mobile phones;

(f) receive and configure processed data from said whiteboard server through a software interface to display said real time daily schedule on said whiteboard display devices in operating rooms; and (g) configure said whiteboard display devices to display a schedule which changes in response to the real time activities of the medical personnel, wherein a portion of at least one of said blocks is highlighted in a first color, and wherein the instructions further cause the first color to be changed to a second color in response to a first condition.

17. The non-transitory computer-readable medium of claim 16, wherein the instructions further cause the one or more processors to operate the mobile applications server to communicate with at least one mobile phone that runs an application that alerts a mobile phone user.

18. The non-transitory computer-readable medium of claim 17, wherein the instructions further cause the one or more processors to cause the application to display a daily schedule of the user.

19. The non-transitory computer-readable medium of claim 16, wherein the instructions further cause the one or more processors to receive and display data on the display devices that is (i) digitally input to said display devices using a tablet computer and (ii) input in an analog manner directly on a display surface of the display devices in operating rooms.

20. The non-transitory computer-readable medium of claim 16, wherein the instructions further cause the one or more processors to configure the display devices to display a schedule for teams of healthcare facility personnel, said teams having been formed from a displayed list of healthcare facility personnel.

21. The non-transitory computer-readable medium of claim 18, wherein the instructions further cause the one or more processors to send an alert automatically to a user in response to specific data input to said mobile applications server.

22. The non-transitory computer-readable medium of claim 16, wherein the instructions further cause the one or more processors to display, on the display devices, breaks taken by said facility employees in real time.

23. A computer-implemented method for managing the display of a real time daily schedule in a healthcare facility, the method comprising:

(a) managing a real time daily schedule for the healthcare facility, said schedule displayed as a series of blocks dynamically affected by real time activities of medical personnel within the healthcare facility;

(b) displaying the schedule on both whiteboard display devices located in operating rooms of the healthcare facility and on displays of mobile phones;

(c) operating a cloud server that maintains a set of data concerning the management of the operating rooms;

(d) operating a digital whiteboard server that receives and processes said set of data for display on the whiteboard display devices;

(e) operating a mobile applications server that processes said set of data for display on the mobile phones;

(f) receiving and configuring processed data from said whiteboard server through a software interface to display said real time daily schedule on the whiteboard display devices in operating rooms; and (g) configuring the whiteboard display devices to display a schedule which changes in response to the real time activities of the medical personnel, wherein a portion of at least one of said blocks is highlighted in a first color, and changing said first color to a second color in response to a first condition.

24. The method of claim 23, further comprising operating the mobile applications server to communicate with at least one mobile phone that runs an application that alerts a mobile phone user.

25. The method of claim 24, further comprising displaying, by the application, a daily schedule of the user.

26. The method of claim 23, further comprising receiving and displaying data on the display devices that is, (i) digitally input using a tablet computer and, (ii) input in an analog manner directly on a display surface of the display devices in operating rooms.

27. The method of claim 23, further comprising configuring the display devices to display a schedule for teams of healthcare facility personnel, said teams having been formed from a displayed list of healthcare facility personnel.

28. The method of claim 25, further comprising automatically sending an alert to the user in response to specific data input to the mobile applications server.

29. The method of claim 23, further comprising displaying, on the display devices, breaks taken by said facility employees.

* * * * *